United States Patent
Mottale et al.

(10) Patent No.: US 6,460,200 B1
(45) Date of Patent: Oct. 8, 2002

(54) SANITARY DEVICE

(76) Inventors: Sima Mottale, Via Lucchini 5, 6900, Lugano (CH); Giordano Basevi, Via Riccardo Pampuri 2, Trivolzio (Pavia) (IT)

(*) Notice: Subject to any disclaimer, the term of this patent is extended or adjusted under 35 U.S.C. 154(b) by 0 days.

(21) Appl. No.: 09/519,958

(22) Filed: Mar. 7, 2000

(30) Foreign Application Priority Data

May 25, 1999 (EP) .............................. 99201650

(51) Int. Cl.⁷ ............................................ A47K 11/00
(52) U.S. Cl. ........................ 4/144.4; 4/144.1; 4/144.2; 4/144.3; 141/331
(58) Field of Search ............................. 4/144.1, 144.2, 4/144.3, 144.4; 141/331, 337, 338

(56) References Cited

U.S. PATENT DOCUMENTS

| | | | |
|---|---|---|---|
| 901,134 A | 10/1908 | Weidl | |
| 1,407,872 A | 2/1922 | Lacy | |
| 2,100,888 A | * 11/1937 | Vine | |
| 2,690,568 A | 10/1954 | Willis | |
| 2,878,486 A | 3/1959 | Bartlett et al. | |
| 3,329,973 A | 7/1967 | Bobbe | |
| 3,571,817 A | 3/1971 | Gosnell | |
| 3,613,122 A | 10/1971 | Gross et al. | |
| 3,804,134 A | * 4/1974 | Wehking | 141/337 |
| 3,956,778 A | 5/1976 | Tanaka | |
| 3,964,111 A | 6/1976 | Packer | |
| 4,023,216 A | * 5/1977 | Li | |
| 4,108,222 A | * 8/1978 | Kaufman | 141/337 |
| 4,305,161 A | 12/1981 | Diaz | |
| 4,608,046 A | 8/1986 | Towfigh | |
| 4,681,573 A | * 7/1987 | McGovern et al. | |
| 4,683,598 A | 8/1987 | Jones | |
| 4,734,941 A | 4/1988 | DeWitt et al. | |
| 4,751,751 A | 6/1988 | Reno | |
| 4,756,029 A | 7/1988 | Zieve et al. | |
| 4,771,484 A | 9/1988 | Mozell | |
| 4,937,890 A | 7/1990 | Tafur | |
| 4,985,940 A | 1/1991 | Jones | |
| 5,091,998 A | 3/1992 | Irazabal | |
| 5,243,712 A | 9/1993 | Cross | |
| 5,370,637 A | 12/1994 | Brodeur | |
| D374,281 S | * 10/1996 | Markles | D24/122 |
| 5,566,400 A | * 10/1996 | Jonee | |
| 5,605,161 A | 2/1997 | Cross | |
| D394,989 S | * 6/1998 | Block | D7/700 |

FOREIGN PATENT DOCUMENTS

| | | | |
|---|---|---|---|
| EP | 0158602 | 10/1985 | |
| EP | 0158602 A1 | * 10/1985 | |
| EP | 0763352 | 3/1997 | |
| EP | WO 97/39706 | * 10/1997 | |
| FR | 2497786 | * 7/1982 | 141/337 |
| GB | 3705 | * 2/1907 | 141/337 |
| WO | 9311691 | 6/1993 | |
| WO | 9739706 | 10/1997 | |
| WO | WO 00/15166 | 3/2000 | |

OTHER PUBLICATIONS www.geniuslady.com/project.htm, Genius Lady 1998.

* cited by examiner

Primary Examiner—David J. Walczak
Assistant Examiner—Khoa Huynh
(74) Attorney, Agent, or Firm—Kalow & Springut LLP

(57) ABSTRACT

A sanitary device enabling women to urinate in an upright position, comprises a foldable tubular body (2) which, in the position intended for use, advantageously assumes the form of a reversed, truncated pyramid comprising an aperture (21) for the collection of urine and an aperture (23) for the release of urine, defined respectively by an upper and a lower edge (3, 4) of said pyramid, aperture (21) for the collection of urine defined as being on a plane substantially perpendicular to a longitudinal axis of said tubular body (2) and preferably as having a substantially quadrangular or rhomboidal shape.

10 Claims, 4 Drawing Sheets

SANITARY DEVICE

FIELD OF APPLICATION

The present invention refers to a sanitary device enabling women to urinate in an upright position.

The invention particularly relates to a sanitary device for women, comprising a foldable tubular body. which, when in use, assumes a substantially funnel-shaped form, to be positioned in a manner adherent to the vulva, in order to receive the urine and direct it away from the body, and thus to permit a woman to urinate conveniently even standing up.

The use of these devices is particularly indicated in public bathrooms and in all hygienically risky situations, where it is preferable to avoid any contact or even proximity between the intimate female parts and surfaces, such as toilet seats, which are dirty and not disinfected, in order to limit the risk of infections or diseases as much as possible.

As known, in the field of intimate feminine hygiene, there is an increasingly felt need for the production of sanitary devices which, on one hand, enable urination in a substantially upright position in a safe and hygienic manner, without risking undesirable leaking or splashing of urine, are easy to apply and occupy an extremely small space when not in use, and on the other hand, are reliable, simple to produce, inexpensive and made of materials which do not pollute the environment.

PRIOR ART

In order to satisfy the above need, proposals have been made in the field for various models of sanitary devices for women comprising a foldable tubular body which, when not in use, has a substantially flat shape, but when in use, expands and assumes an approximately funnel-shaped form.

Therefore, in the position intended for use, the tubular body has a first aperture of large diameter, to be applied in contact with the vulva so as to include the external orifice of the urethra and thus to collect the urine coming from the bladder, and a second aperture of smaller diameter than the first one, for the release of urine from the device and its suitable direction into the toilet bowl.

For example, U.S. Pat. No. 4,023,216 describes a device of the type indicated above, obtained through the folding of a sheet of water-repellent material along a plurality of folding lines.

Such a device presents four side walls of various lengths, so as to obtain an aperture for the collection of urine that is oblong and transversal relative to the axis of the device. In addition, in order to guarantee sufficient adherence of the device to the vulva, and thus to avoid undesirable leakage of urine, the device provides a semicircular tab—which can be folded back upon itself—extending from the two longer walls. When in use, the tab is raised at an angle greater than 90° relative to the longer walls and is made adhere to the vulva, together with the upper edge of the two shorter walls.

Although advantageous in some aspects, the device just described presents a series of drawbacks as described below.

First of all, the fact that the aperture for the collection of urine is transversal relative to the axis of the device causes the device, in use, to take a position up, which is almost horizontal relative to the position of the body. This has the result of making it extremely difficult to control the stream of urine released from the device so that the urine flows precisely into the toilet bowl.

In other words, the structure of the sanitary device when in use does not permit the simple and reliable control of the trajectory of the urine stream, which inevitably varies as a function of the pressure and rate of the flow of urine from the urethra.

In this connection, it is actually debatable whether the user, even after long practice, is able to use the device according to the prior art in an acceptable manner, without soiling the toilet.

This drawback drastically limits its use, making it fit for wall-type toilets (public urinals) only.

An additional drawback of the sanitary device according to the prior art is that of its highly complex structure and manufacture, which results from the presence of walls of variable length and conformation and from the necessity for transversal fold lines in order to accomplish a correct opening of the semicircular tab, with consequently high production costs.

In addition, the use of such a device is particularly complicated and elaborate. Several operations, involving the use of both hands, are necessary in order to be able to open the device correctly. Once it has been opened, it operates in one position only, and therefore cannot be immediately used, as it may require to be first turned in the correct direction. Because of its nearly horizontal position, the correct application of the sanitary device in the pubic area requires a certain amount of practice.

Moreover, it is necessary to ascertain absolutely that the semicircular tab is completely raised before use, in order to prevent the pressure exerted against the pubic area, with a view to ensuring the necessary adherence of the device, from causing the tab to fold back upon itself, thus causing leakage of urine.

Finally, it should be noted that the absence of a longitudinal fold line with respect to the shorter walls, makes the correct opening of the sanitary device difficult, as it requires the exertion of a high, but nonetheless controlled, force against the side edges of the device when the latter is in the flat position, along with a certain degree of dexterity.

Precisely due to these disadvantages, sanitary devices according to the prior art, intended to enable women to urinate in an upright position, have not found practical application to date, notwithstanding the ever-growing need in the field of intimate feminine hygiene.

SUMMARY OF THE INVENTION

The problem underlying the present invention is that of providing a sanitary device which enables urination by women in an upright position, in a simple, reliable and extremely hygienic manner, and which, at the same time, is practical, simple and inexpensive to produce.

The above problem is solved, according to the invention, by a sanitary device which comprises a foldable tubular body which, in the position intended for use, assumes the form of a reversed, truncated pyramid comprising an aperture for the collection of urine and an aperture for the release of urine, defined respectively by an upper and a lower edge of the pyramid, the aperture for the collection of urine defined as being on a plane substantially perpendicular to a longitudinal axis of the tubular body and preferably as having a substantially quadrangular or rhomboidal shape.

In particular, this problem is solved by a sanitary device of the type described above, obtainable by folding a sheet having four fold lines which extend longitudinally on the sheet and subdivide it into five sections: a first section defined between a first side end of the sheet and a first fold line, which serves as a side closure tab of the tubular body;

and second, third, fourth and fifth sections, substantially trapezoidal in shape and symmetrical with respect to each other, defined by the first and a second fold line, by the second and a third fold line, by the third and a fourth fold line, and by the fourth fold line and a second side end of the sheet, respectively, and serving as side walls of the tubular body, the first section being attached to the fifth section with the second end of the sheet arranged so as to correspond to the first fold line.

As will be seen in greater detail in the description below, the present invention enables the achievement of a foldable sanitary device with the aperture for the collection of urine substantially perpendicular to the longitudinal axis of the device, thus providing the advantage of extreme ease, safety and practicality of use.

According to a further aspect thereof, the present invention also concerns a method for the manufacture of a sanitary device enabling urination by women in an upright position, as claimed in Claim 9.

The features and advantages of the invention will be clear from the following indicative and non-limiting description of an embodiment of the invention, made with reference to the attached drawings.

DETAILED DESCRIPTION OF A PREFERRED EMBODIMENT

With reference to FIGS. 1–5, a sanitary device enabling women to urinate in an upright position, according to a preferred embodiment of the present invention, is indicated in its whole with 1.

Figure 1:
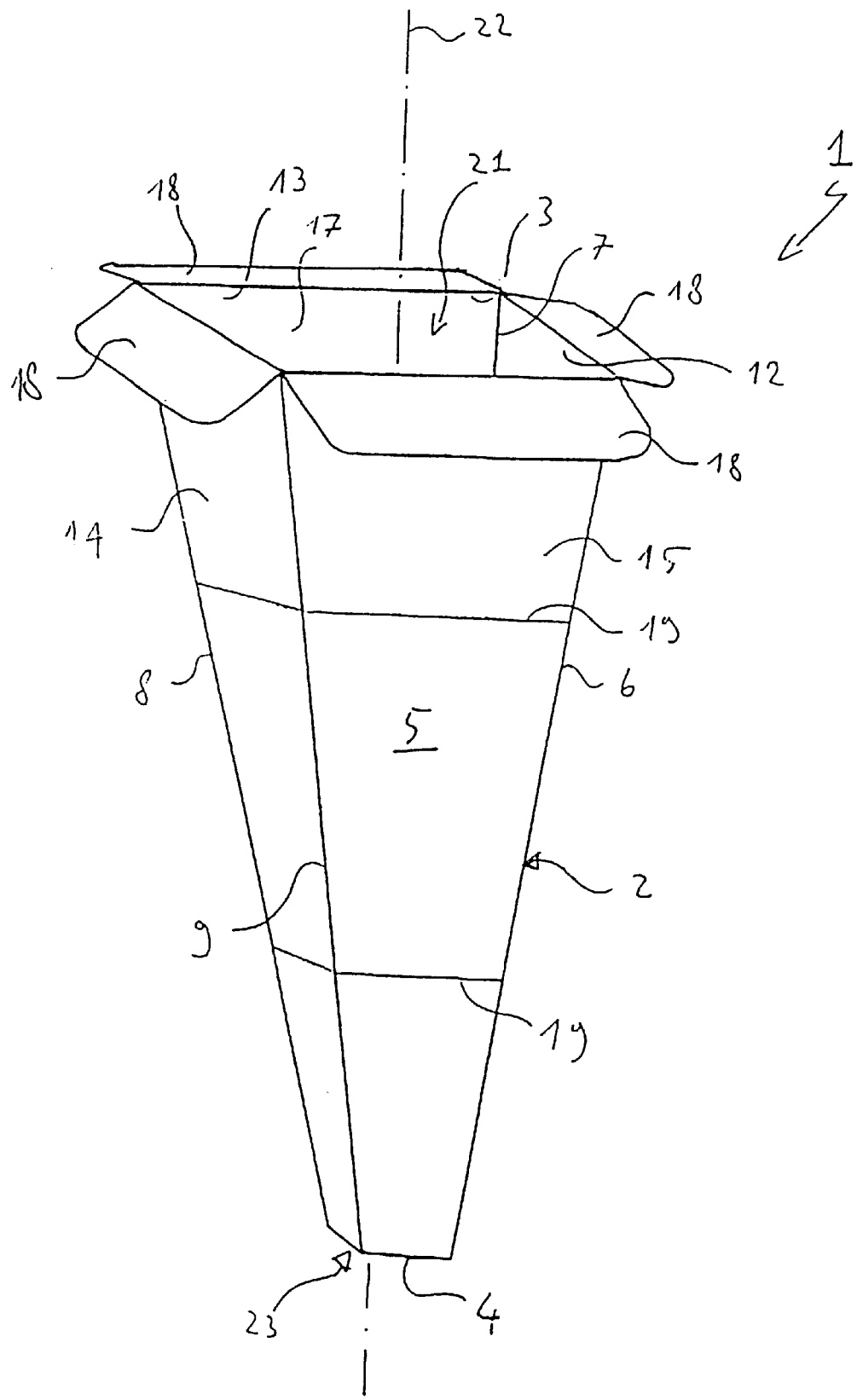
FIG. 1 shows a schematic perspective view of the sanitary device, in the position intended for use, according to a preferred embodiment of the present invention.

The sanitary device 1 comprises a foldable tubular body 2, which—as shown in FIG. 1—advantageously assumes, when in use, the form of a reversed, truncated pyramid, with apertures at an upper edge 3 and a lower edge 4.

According to a particularly advantageous aspect of the present invention, tubular body 2 may be obtained by folding a sheet 5 with four fold lines, indicated respectively by reference numerals 6–9, which extend longitudinally over sheet 5, subdividing it into five sections.

Figure 3:
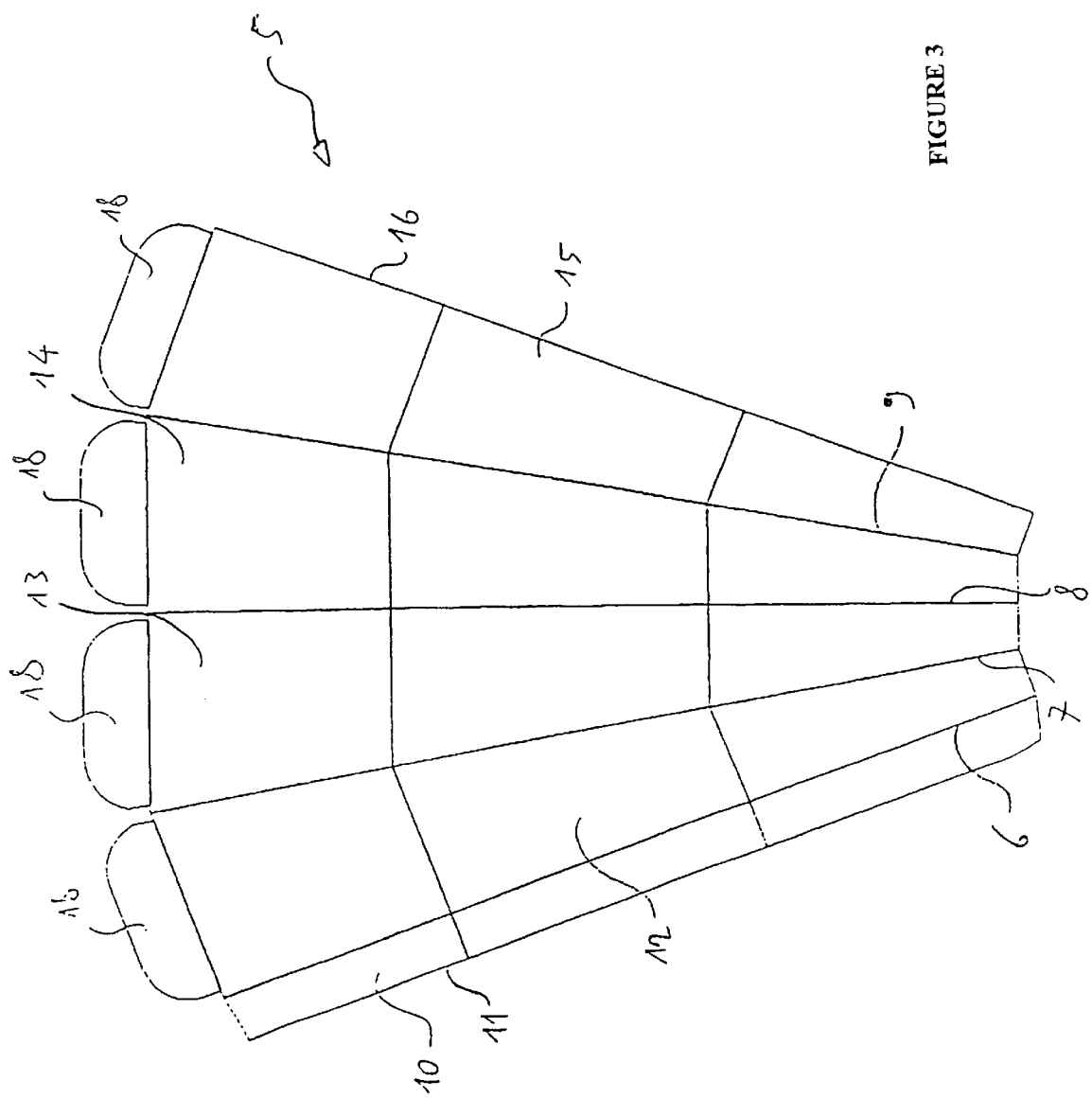
FIG. 3 shows a schematic front view of a sheet for obtaining the sanitary device of FIG. 1.

In the example shown in FIG. 3, the fold lines 6–9 divide sheet 5 into: a first section 10 defined between a first side end 11 of sheet 5 and first fold line 6; a second section 12 defined between the fold line 6 and the second fold line 7; a third section 13 defined between the fold line 7 and the third fold line 8; a fourth section 14 defined between the fold line 8 and the fourth fold line 9; and finally, a fifth section 15 defined between the fold line 9 and a second side end 16 of sheet 5.

First section 10, remarkably smaller than the other sections 12–15, serves as a tab intended for the side closure of tubular body 2. Sections 12–15 serve as side walls of said tubular body.

It should be noted that sections 12–15 are substantially symmetrical with respect to each other and are of trapezoidal shape. In other words, the various sections 12–15 are practically identical, all having substantially the same dimensions and shape.

Figure 2:
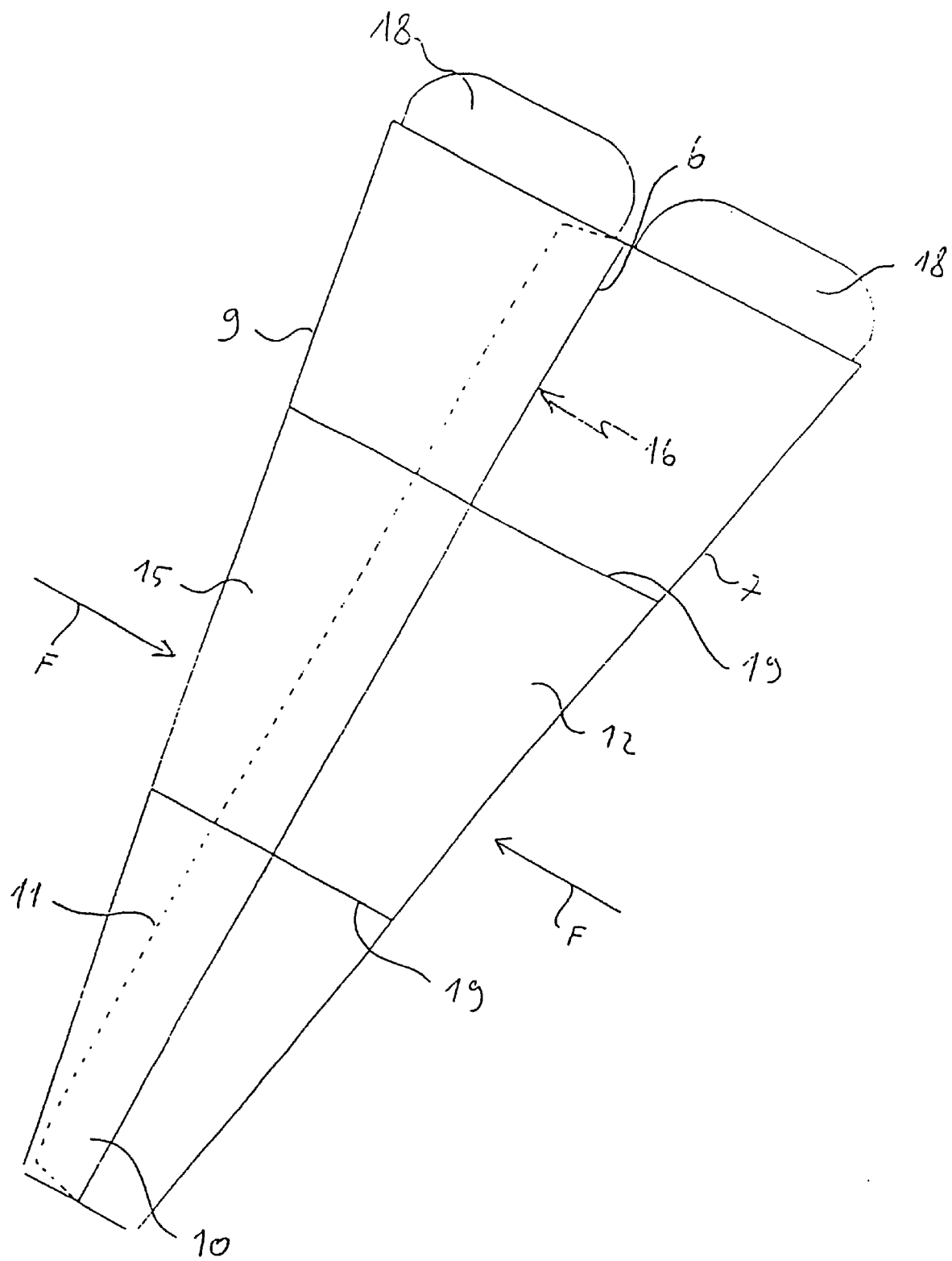
FIG. 2 shows a schematic front view of the sanitary device shown in FIG. 1, not in use.

Advantageously, in the sanitary device 1, the first section 10 is attached to the fifth section 15 with the second end 16 of sheet 5 arranged so as to correspond to the first fold line 6, as indicated in FIG. 2.

When not in use, as shown in FIG. 2, tubular body 2 is flattened between the second and fourth fold lines 7, 9, with the second and fifth sections 12, 15, advantageously facing the third and fourth sections 13, 14.

In order to shift the device from the position not intended for use to the position intended for use, it is enough to exert a slight manual pressure on the side edges of tubular body 2, which correspond to fold lines 7 and 9 as indicated by Arrow F in FIG. 2, in order for said tubular body to open and become the truncated pyramid shown in FIG. 1.

The device according to the present invention enables women to urinate in an upright position in an extremely simple and reliable manner and under optimal hygienic conditions, thus overcoming all of the drawbacks present in the devices according to the prior art.

In fact, the sanitary device according to the invention provides—among others—the following advantages.

When in use, the sanitary device is in the form of a reversed, truncated pyramid, with the four side walls 12–15 substantially symmetrical with respect to each other, and therefore, with the aperture 21 for the collection of urine defined on a plane substantially perpendicular to the longitudinal axis 22 of tubular body 2.

This advantageously permits the simple, precise and effective positioning of the sanitary device according to the invention in contact with the vulva, and at the same time, the convenient direction of the flow of urine into the toilet bowl.

Aperture 21 for the collection of urine, when the sanitary device is in the position intended for use, may be uniformly applied in contact with the vulva by means of a simple, direct upward movement. The strength of the pressure to be exerted against the vulva may be regulated at will, in order to prevent the leakage of urine.

On the contrary, in the above mentioned device according to the prior art, the aperture for the collection of urine—which is arranged diagonally relative to the side walls of the sanitary device—makes the application of said device problematic and it becomes difficult to regulate the force to be exerted against the vulva and thus to ensure that the device is uniformly held in place.

In addition, it is now possible to arrange the tubular body 2 in a substantially vertical position relative to the position of the user's body, with lower aperture 23 for the release of urine positioned directly above the toilet bowl, thus enabling optimal, precise control of the flow of urine leaving the sanitary device, irrespective of the pressure and rate of the flow of urine from the urethra. The present device can thus be advantageously used in any situation and in any type of toilet.

Finally, it should be noted that the reversed pyramidal shape, with the increasing width of the side walls, gives the device an optimal grip and prevents the hand holding the device from slipping upward when the device is pressed against the vulva, thus facilitating adherence and enabling use of the device even when the user's hand is wet or sweaty.

The sanitary device according to the present invention may be advantageously operated with one hand only, and does not require the use of both hands for opening the device from the position not intended for use to the position intended for use, or for holding the device in place during urination.

In fact, it is possible to perform, with only one hand and in an extremely simple matter, all operations related to the use of the device. Removal of the sanitary device from its envelope or suitable container, where the device is in a flattened position of non use; opening the device into the position intended for use, by means of a slight pressure on the side walls (corresponding to fold lines 7 and 9); and positioning the device in contact with the vulva.

This feature is particularly useful and advantageous, as it enables the user to have one hand free at all times, in order—for example—to hold up her clothing during urination, thus enabling rapid and effective action even in small spaces and in emergency situations.

In addition, the particular shape of aperture 21 for the collection of urine renders the device operative irrespective of the side from which it is grasped, thus advantageously increasing the practicality of its use.

Thanks to its reversed, truncated pyramidal shape, with the aperture 21 for the collection of urine substantially square or rhomboidal in form, the sanitary device according to the invention is extremely stable and solid when in use, with no risk of structural collapse, and does not necessitate any particular attention or sensitivity to the pressure which must be exerted in order to keep the device open and in contact with the vulva.

This is due, not only to the geometric structure of the device, but also to the fact that the first fold line 6, which delimits the joint between the section 15 and the side closure tab 10, is centrally arranged between the side edges of the device when not in use (fold lines 7 and 9).

In the position not intended for, the sanitary device advantageously occupies a particularly small space, and may be flattened to the point of obtaining a sheet substantially trapezoidal in shape, with the side walls overlapping each other (see FIG. 2).

In this way, the storage of sanitary devices in closed position (not intended for use) does not create particular problems of space, and a large number of devices can be stored in small volumes—for example, in suitable containers or dispensers which may be carried with the user, or provided in public toilets.

Further on, the absence of protrusions, indentations or parts folded back upon themselves facilitates the storage and extraction of the devices in/from suitable containers.

The sanitary device according to the invention may be manufactured with substantially any type of material sufficiently flexible to enable the device to be opened and closed along the appropriate fold lines.

For clear reasons of hygiene, it is preferable for the sanitary device to be of the disposable type, which may be dispersed into the environment after use.

It is thus preferable to manufacture the device of biodegradable materials, such as for example cellulose-based materials, either natural or treated with an impermeable coating, which are sufficiently water-repellent to enable urination without undesirable leakage of liquids.

In this respect, particularly satisfactory results are obtained through the use of cardboard suitable for the food industry for tubular body 2.

This material, in addition to being easily available on the market and inexpensive, features good mechanical characteristics of strength and flexibility which render it suitable for use as a foldable tubular body, and at the same time has a surface which, in its natural state, is impermeable to urine and thus does not require any particular waterproofing.

Moreover, cardboard suitable for the food industry does not cause allergies and is sufficiently aseptic to guarantee optimal hygienic conditions for the user.

Finally, the sanitary device according to the invention may be obtained in an extremely simple manner and with low production costs.

To this end, the present invention advantageously provides a method for the production of the sanitary device represented in FIGS. 1–5, in order to facilitate urination by women in an upright position, which comprises the steps of:

providing a sheet 5, preferably of degradable material, substantially trapezoidal in shape or in the form of a sector of an annulus;

effecting four longitudinal fold lines on sheet 5, which subdivide it into five sections: a first section 10 defined between a first side end 11 of sheet 5 and a first fold line 6, which serves as a side closure tab for the sanitary device; and second, third, fourth and fifth sections 12–15, substantially trapezoidal in shape and symmetrical with respect to each other, defined by the first and a second fold line, 6–7; by the second and a third fold line, 7–8; by the third and a fourth fold line, 8–9; and by the fourth fold line 9 and a second side end 16 of sheet 5, and serving as side walls of the sanitary device;

folding the sheet 5 along second and fourth fold lines 7, 9, and attaching the first section 10 to the fifth section 15 with the second end 16 of sheet 5 arranged so as to correspond to first fold line 6, so as to obtain a foldable tubular body 2, having a substantially trapezoidal shape in the position not intended for use and a reversed, truncated pyramid open at an upper edge 3 and at a lower edge 4, in the position intended for use.

It is clear that the steps for the manufacture of the present sanitary device are particularly simple to be carried out and do not require special or exceptionally complex machinery, leading to an advantage in terms of investments and operative costs.

For example, the sheet 5, suitably shaped with the four fold lines, may be obtained through punching while the steps of folding and closure of the side walls may be obtained through mechanical movements conventional per se.

In order to attach the closure tab 10 to section 15 of tubular body 2, glue of a conventional type—natural or synthetic, soluble or insoluble in water—may be used, as well as techniques such as heat-welding, stitching or stapling.

To this end, according to the preferred embodiment represented in the attached figures and shown in FIG. 2 by dotted lines 11, first section 10 is advantageously attached to the fifth section 15 along an internal surface 17 of tubular body 2.

In particular, the method for the manufacture of the sanitary device according to the invention provides for the step of attaching the section 10 to said internal surface 17.

By doing so, particularly satisfactory results are obtained with regard to the firmness of the side closure, which it has been found to be more hermetic and resistant than an external attachment of first section 10 to section 15.

The internal attachment of section 10 is also technically easier to implement with mechanical systems and presents fewer hygiene-related problems than a closure on the external surface of the tubular body 2.

In order to ensure a more delicate contact with the vulva, the device according to the present invention provides for at least one sealing tab 18 foldable in an outward direction, extending from said upper edge 3 of the tubular body 2 as a portion of one of said second to fifth sections 12–15.

As shown in FIGS. 1 and 3, device 1 preferably comprises four sealing tabs, all indicated by 18, one for each of sections 12–15, respectively.

To this end, the method for the manufacture of the sanitary device according to the invention provides for the step of providing a sheet 5, substantially trapezoidal in shape or in the form of a sector of an annulus, comprising at least one foldable sealing tab 18 extending as a portion of one of sections 12–15.

Figure 4:
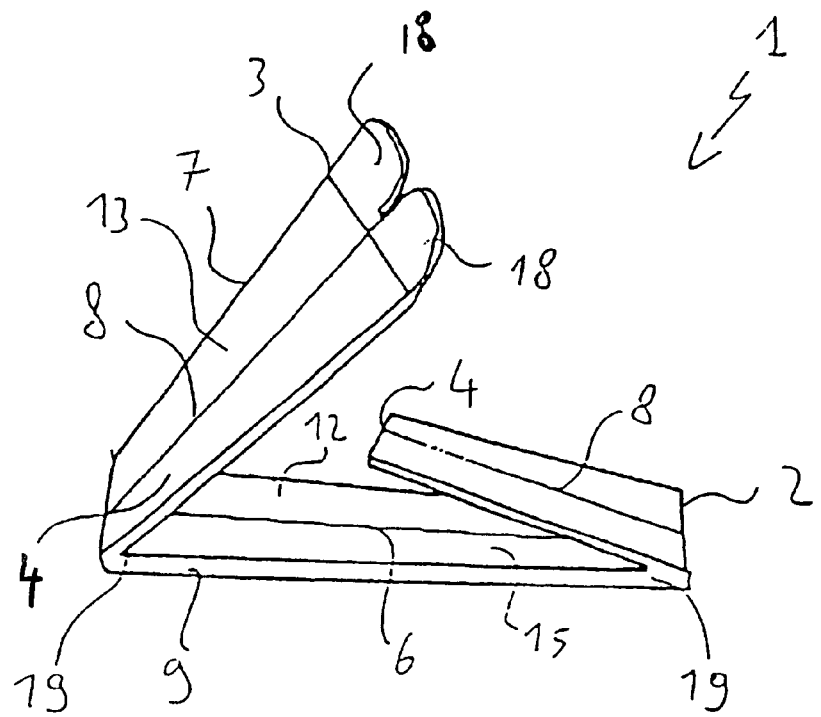
FIG. 4 shows a schematic perspective view of the sanitary device shown in FIG. 2, folded upon itself according to the preferred embodiment.

In FIGS. 1–4, the numeral 19 indicates two transversal fold lines (horizontal in this particular example) extending around the entire perimeter of tubular body 2, in order to enable the latter to be folded back upon itself in the position not intended for use, as shown in FIG. 4.

In this way, it is possible to drastically reduce the longitudinal dimension of the sanitary device when not in use, enabling the device to be carried with the user, even in a pocket, or placed in small handbags.

Figure 5:
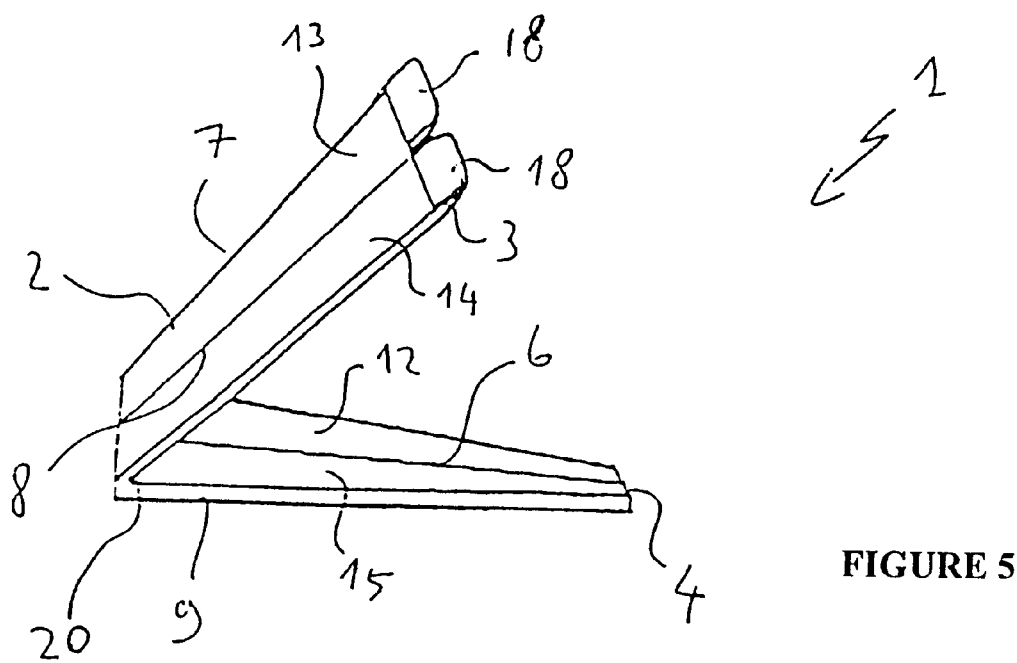
FIG. 5 shows a schematic perspective view of the sanitary device shown in FIG. 2, folded upon itself according to a further embodiment.

According to a further embodiment of the invention, the sanitary device has a single transversal (preferably horizontal) fold line, arranged at about half the height of tubular body 2 and indicated in FIG. 5 by numeral 20.

Finally, it is important to note that studies performed by the applicants have shown that it is particularly advantageous—with regard to both practicality of use and mechanical resistance—to manufacture a sanitary device comprising a tubular body 2, the width of whose side walls defined by sections 12–15, measured along upper edge 3, is 2 to 10 times, preferably 4 to 6 times, that of their width measured along lower edge 4.

What is claimed is:

1. A method for disposing urine which enables a woman to urinate in an upright position, comprising;

(a) providing a female urinary device comprising a foldable tubular body which, in the position intended for use, has a reversed, truncated pyramid shape with four longitudinal edges, opposite two-by-two, defined between respective side walls of said foldable tubular body and wherein the sanitary device has a first aperture for the collection of urine and a second aperture for the release of urine, defined respectively by an upper and a lower edge of said reversed, truncated pyramid, the first aperture for the collection of urine having a substantially square or rhomboidal shape and being on a plane substantially perpendicular to a longitudinal axis of said tubular body, and wherein said device comprises four sealing tabs, one at each side of said first aperture on said reversed, truncated pyramid shape, and wherein said tabs act to prevent leaks through the upper edge of said first aperture;

(b) directly holding the female urinary device along two opposite edges of said longitudinal edges of said foldable tubular body; and, (c) positioning the first aperture of the female urinary device in contact with a vulva and applying a predetermined pressure to the vulva by pressing an upper edge of said first aperture against the vulva to prevent leaks and to enable urine to be released through the second aperture.

2. A method according to claim 1, wherein said sealing tabs have rounded edges.

3. A method for disposing urine which enables a woman to urinate in an upright position, comprising:

(a) providing a female urinary device that enables women to urinate in an upright position, the device comprising a foldable tubular body which, in the position intended for use, has a reversed, truncated pyramid shape with four longitudinal edges, opposite two-by-two, defined between respective side walls of said foldable tubular body, open at an upper and a lower edge and obtainable by folding a sheet, along four fold lines which extend longitudinally on said sheet and which subdivide it into five sections: a first section defined between a first side end of the sheet and a first fold line, the first section serving as a side closure tab of the tubular body; and a second, third, fourth and fifth section, each substantially trapezoidal in shape and symmetrical with respect to each other, the second, third, fourth and fifth sections defined by said first and a second fold line, by said second and a third fold line, by said third and a fourth fold line, and by said fourth fold line and a second side end of said sheet, respectively, and these sections serving as side walls of said tubular body, said first section being attached to said fifth section with the second end of the sheet arranged so as to correspond to said first fold line, and wherein said device comprises four sealing tabs, one at each side of said first aperture on said reversed, truncated pyramid shape, and wherein said tabs act to prevent leaks through the upper edge of said first aperture;

(b) positioning the upper edge of the female urinary device in contact with a vulva, and holding the female urinary device along two opposite edges of said longitudinal edges of said foldable tubular body; and (c) positioning the first aperture of the female urinary device in contact with the vulva and applying a predetermined pressure to the vulva by pressing the upper edge of said first aperture against the vulva to prevent leaks and to enable urine to be released through the second aperture.

4. A method according to claim 3, wherein said first section of the device is attached to said fifth section along an internal surface of tubular body.

5. A method according to claim 3, wherein said tubular body, when not in use, is flattened between said second and fourth fold lines, with the second and fifth sections facing the third and fourth sections, respectively.

6. A method according to claim 3, wherein said tubular body comprises at least one transversal fold line, extending along the entire perimeter of said tubular body, enabling said tubular body to be folded back on itself when not in use.

7. A method according to claim 6, wherein said transversal fold line is horizontal.

8. A method according to claim 3, wherein the width of said second to fifth sections, measured along said upper edge of the tubular body, is 2 to 10 times that of the width of the same sections measured along said lower edge.

9. A method according to claim 8, wherein the width of said second to fifth sections, measured along said upper edge of the. tubular body is 4 to 6 times that of the width of the same sections measured along said lower edge.

10. A method according to claim 3, wherein said sealing tabs have rounded edges.

* * * * *